US009456742B2

(12) United States Patent  (10) Patent No.: US 9,456,742 B2
Muto  (45) Date of Patent: Oct. 4, 2016

(54) OPHTHALMOLOGIC APPARATUS

(71) Applicant: CANON KABUSHIKI KAISHA, Tokyo (JP)

(72) Inventor: Kenji Muto, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 54 days.

(21) Appl. No.: 13/651,632

(22) Filed: Oct. 15, 2012

(65) Prior Publication Data

US 2013/0107213 A1    May 2, 2013

(30) Foreign Application Priority Data

Oct. 27, 2011  (JP) .................................. 2011-236014

(51) Int. Cl.
*A61B 3/10*  (2006.01)
*A61B 3/00*  (2006.01)
(Continued)

(52) U.S. Cl.
CPC .............. *A61B 3/102* (2013.01); *A61B 3/0075* (2013.01); *G01B 9/0203* (2013.01); *G01B 9/02044* (2013.01); *G01B 9/02068* (2013.01); *G01B 9/02091* (2013.01); *A61B 5/0066* (2013.01)

(58) Field of Classification Search
CPC ................. G06T 2207/30041; G06T 11/003; G06T 2207/10101; G06T 2207/10072; A61B 3/113; A61B 3/12; A61B 3/152; G01B 9/02044; G01B 9/02048; G01B 9/02091
USPC ........ 351/206, 246, 208; 382/117, 131, 173; 359/450, 479, 497; 348/78; 356/479
See application file for complete search history.

(56) References Cited

U.S. PATENT DOCUMENTS 7,668,351 B1 *  2/2010  Soliz et al. ................... 382/128
7,695,139 B2     4/2010  Ishikura
(Continued)

FOREIGN PATENT DOCUMENTS

CN     1989894 A     7/2007
CN   101674770 A     3/2010
(Continued)

OTHER PUBLICATIONS

Kok-Lim Low, "Linear Least-Squares Optimization for Point-to-Plane ICP Surface Registration", Dept. of Computer Science, University of North Carolina at Chapel Hill, Feb. 2004.*
(Continued)

*Primary Examiner* — Bumsuk Won
*Assistant Examiner* — Collin X Beatty
(74) *Attorney, Agent, or Firm* — Fitzpatrick, Cella, Harper & Scinto

(57) ABSTRACT

In order to take a good tomographic image without a complicated position adjustment operation by an inspector, an ophthalmologic apparatus is provided which acquires a fundus tomographic image by optical coherence tomography utilizing interference by low coherence light. The ophthalmologic apparatus includes a tomographic image acquiring unit for acquiring a tomographic image of an eye to be inspected, a tilt calculation unit for calculating a tilt of the tomographic image, and a relative position changing unit for changing a relative position between the tomographic image acquiring unit and the eye to be inspected based on the tilt of the tomographic image. An evaluation index may be devised that indicates a problem with the tomographic image or an anterior ocular image and the relative position changing means may change the relative position according to this evaluation index. The evaluation index is linked to the tilt of the tomographic image.

15 Claims, 6 Drawing Sheets

(51) Int. Cl.
  *G01B 9/02* (2006.01)
  *A61B 5/00* (2006.01)

(56) References Cited

U.S. PATENT DOCUMENTS

| | | |
|---|---|---|
| 7,954,948 B2 | 6/2011 | Nozato et al. |
| 8,204,300 B2 | 6/2012 | Sugita et al. |
| 8,308,297 B2 | 11/2012 | Hirose et al. |
| 8,317,326 B2 | 11/2012 | Nozato et al. |
| 8,384,908 B2 | 2/2013 | Sugita et al. |
| 9,055,892 B2 | 6/2015 | Narasimha-Iyer et al. |
| 2003/0190091 A1* | 10/2003 | Stewart et al. ............... 382/294 |
| 2004/0258285 A1* | 12/2004 | Hansen et al. ............... 382/128 |
| 2007/0146636 A1 | 6/2007 | Ishikura |
| 2007/0195269 A1* | 8/2007 | Wei et al. ............... 351/221 |
| 2008/0055543 A1 | 3/2008 | Meyer et al. |
| 2008/0100612 A1 | 5/2008 | Dastmalchi et al. |
| 2009/0103049 A1* | 4/2009 | McLean et al. ............... 351/206 |
| 2009/0316112 A1* | 12/2009 | Neal et al. ............... 351/246 |
| 2010/0061601 A1* | 3/2010 | Abramoff et al. ............... 382/117 |
| 2010/0165289 A1 | 7/2010 | Nozato et al. |
| 2010/0166280 A1* | 7/2010 | Endo et al. ............... 382/131 |
| 2010/0166293 A1* | 7/2010 | Sugita et al. ............... 382/154 |
| 2010/0220914 A1* | 9/2010 | Iwase et al. ............... 382/131 |
| 2010/0226542 A1* | 9/2010 | Everett et al. ............... 382/106 |
| 2010/0321700 A1 | 12/2010 | Hirose et al. |
| 2011/0007321 A1* | 1/2011 | Everett et al. ............... 356/479 |
| 2011/0007957 A1* | 1/2011 | Sakagawa ............... 382/131 |
| 2011/0137157 A1* | 6/2011 | Imamura et al. ............... 600/425 |
| 2011/0149239 A1* | 6/2011 | Neal et al. ............... 351/205 |
| 2011/0199579 A1* | 8/2011 | Muto ............... 351/206 |
| 2011/0205490 A1* | 8/2011 | Murata et al. ............... 351/206 |
| 2011/0205550 A1 | 8/2011 | Nozato et al. |
| 2011/0213342 A1* | 9/2011 | Tripathi et al. ............... 604/541 |
| 2011/0228221 A1* | 9/2011 | Hanebuchi et al. ............... 351/206 |
| 2011/0228222 A1* | 9/2011 | Kobayashi ............... 351/206 |
| 2011/0234785 A1* | 9/2011 | Wanda et al. ............... 348/78 |
| 2011/0243408 A1* | 10/2011 | Takama ............... 382/128 |
| 2011/0243415 A1* | 10/2011 | Yonezawa et al. ............... 382/131 |
| 2011/0267340 A1* | 11/2011 | Kraus ............... A61B 3/102 345/419 |
| 2011/0275931 A1* | 11/2011 | Debuc ............... 600/425 |
| 2011/0286003 A1 | 11/2011 | Ono |
| 2011/0299034 A1* | 12/2011 | Walsh et al. ............... 351/206 |
| 2012/0218557 A1 | 8/2012 | Sugita et al. |
| 2012/0249961 A1 | 10/2012 | Muto |
| 2012/0249962 A1* | 10/2012 | Uchida ............... 351/208 |
| 2012/0274897 A1 | 11/2012 | Narasimha-Iyer et al. |
| 2012/0320338 A1 | 12/2012 | Hirose et al. |

FOREIGN PATENT DOCUMENTS

| | | |
|---|---|---|
| CN | 103491857 A | 1/2014 |
| JP | 2008-298767 A | 12/2008 |
| JP | 2010-151713 A | 7/2010 |
| JP | 2010-181172 A | 8/2010 |
| JP | 2011-087672 A | 5/2011 |
| JP | 2011-092290 A | 5/2011 |
| JP | 2014-512239 A | 5/2014 |
| WO | 2011/111376 A1 | 9/2011 |
| WO | 2012/146711 A2 | 11/2012 |

OTHER PUBLICATIONS

Thomas Martini Joergensen, Bjarne Ersboell, Birgit Sander, and Michael Larsen. Reducing speckle noise in retinal OCT images by aligning multiple B-scans. Proceedings of SPIE vol. 5316 (SPIE, Bellingham, WA, 2004). doi: 10.1117/12.529158.*

Amirhossein Hariri, et al., "Effect of Angle of Incidence on Macular Thickness and Volume Measurements Obtained by Spectral-Domain Optical Coherence Tomography", Investigative Ophthalmology & Visual Science, vol. 53, No. 9, Aug. 2012, pp. 5287-5291.

Brandon J. Lujan, et al., "Revealing Henle's Fiber Layer Using Spectral Domain Optical Coherence Tomography", Investigative Ophthalmology & Visual Science, vol. 52, No. 3, Mar. 2011, pp. 1486-1492.

Mar. 1, 2013 European Search Report in European Patent Appln. No. 12189103.0.

D.M. Stein, et al., "A new quality assessment parameter for optical coherence tomography", British Journal of Ophthalmology, vol. 90, 2006, pp. 186-190.

Jul. 2, 2014 Chinese Official Action in Chinese Patent Appln. No. 201210421565.8.

Apr. 15, 2015 Chinese Official Action in Chinese Patent Appln. No. 201210421565.8.

* cited by examiner

OPHTHALMOLOGIC APPARATUS

BACKGROUND OF THE INVENTION

1. Field of the Invention

The present invention relates to an ophthalmologic apparatus.

2. Description of the Related Art

In recent years, an apparatus using optical coherence tomography (OCT) (hereinafter referred to also as an OCT apparatus) has been used practically, which utilizes interference caused by low coherence light to take tomographic images. This apparatus can take a tomographic image with a resolution corresponding to approximately a wavelength of light entering into an object to be inspected, and hence the tomographic image of the object to be inspected can be obtained with high resolution. The OCT apparatus is particularly useful as an ophthalmologic apparatus for acquiring a tomographic image of a retina on an eye fundus.

It is generally useful to bring an inspection portion of the apparatus (such as a measurement optical system) into alignment with respect to an eye to be inspected.

Japanese Patent Application Laid-Open No. 2010-181172 describes an optical image measurement apparatus as the OCT apparatus which takes a tomographic image automatically in a state of good alignment.

Here, Japanese Patent Application Laid-Open No. 2010-181172 mentions automatic alignment for an eye to be inspected, but has no detailed description on a specific configuration.

The alignment for an eye to be inspected is often performed by detecting a pupil center position of an anterior ocular segment of the eye and by aligning the optical axis of an inspection portion to this detected position, regardless of manual or automatic alignment. However, in this case, depending on a characteristic of the eye to be inspected, there is a possibility of being the tomographic image of the fundus dark. In this case, the inspector is required to perform fine adjustment of a position of the optical axis of the inspection portion so that the fundus tomographic image is improved. This operation is complicated for the inspector.

SUMMARY OF THE INVENTION

In view of the above-mentioned background, it is desired to adjust automatically a positional relationship between an eye to be inspected and a unit for acquiring an image of the eye to be inspected so that a good tomographic image can be taken.

Note that, without limiting to the above-mentioned desire, it is also desirable to achieve action and effect that are derived from each configuration of an embodiment of the present invention described later and cannot be achieved by conventional technologies.

In view of the above-mentioned problem, according to an exemplary embodiment of the present invention, there is provided an ophthalmologic apparatus, comprising: a tomographic image acquiring unit for acquiring a tomographic image of an eye to be inspected; a tilt calculation unit for calculating a tilt of the tomographic image; and a relative position changing unit is configured to change a relative position between the tomographic image acquiring unit and the eye based on the tilt of the tomographic.

Further, according to another exemplary embodiment of the present invention, there is provided an ophthalmologic apparatus as a fundus inspection apparatus for inspecting a fundus of an eye to be inspected, comprising: a measurement optical system for acquiring an anterior ocular image and a tomographic image of the fundus; a moving unit for moving the measurement optical system; a movement control unit for controlling the moving unit; an evaluation index calculation unit for calculating an image evaluation index value of the tomographic image; and an image comparing unit for comparing the image evaluation index value with a target value, wherein the movement control unit is configured to adjust a movement amount based on a result of comparison performed by the image comparing unit. According to further exemplary embodiments of the present invention, there are provided an ophthalmologic method comprising: acquiring a tomographic image of an eye to be inspected using a tomographic image acquiring means; calculating a tilt of the tomographic image; and changing a relative position between the tomographic image acquiring means and the eye to be inspected based on the tilt of the tomographic image.

According to the present invention, the positional relationship between the eye to be inspected and the unit for acquiring an image of the eye to be inspected can be adjusted automatically in the hope that a good tomographic image can be taken.

Further features of the present invention will become apparent from the following description of exemplary embodiments with reference to the attached drawings.

DESCRIPTION OF THE EMBODIMENTS

First Embodiment

An ophthalmologic apparatus (also known as a fundus inspection apparatus) of this embodiment, which is an OCT apparatus having an automatic alignment function, can automatically determine a position where a good tomographic image can be taken and can continuously perform the automatic alignment at the position.

(Schematic Configuration of Apparatus)

Figure 2A:
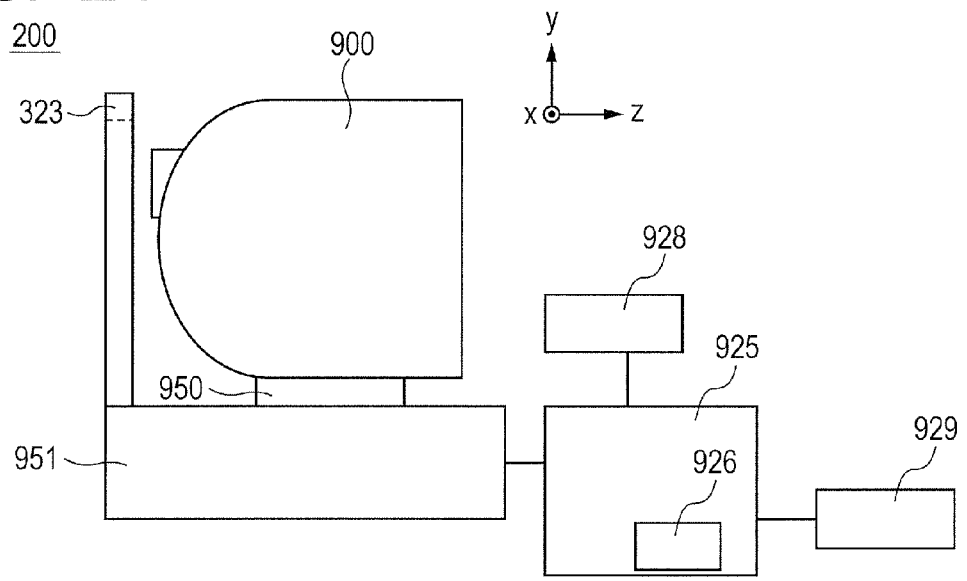
FIG. 2A is a diagram illustrating a main configuration of a fundus inspection apparatus according to the first embodiment.

A schematic configuration of the fundus inspection apparatus according to this embodiment is described with reference to FIG. 2A. FIG. 2A is a side view of an ophthalmologic apparatus 200, which includes an optical head 900 as a measurement optical system for taking an anterior ocular image, a two-dimensional image and a tomographic image of a fundus; and a stage portion 950 as a moving unit enabling the optical head to move in x, y, and z directions in FIG. 2A using a motor (not shown). The ophthalmologic apparatus 200 also includes a base portion 951 incorporating a spectroscope described later. The optical head 900 acquires the anterior ocular image and the tomographic image of the fundus of the eye to be inspected in its role as the measurement optical system of the present invention, and functions as a tomographic image acquiring unit. A personal computer 925, which also works as a control unit of the stage portion, controls the stage portion 950 and organizes the tomographic image in its role as a movement control unit in the present invention. A hard disk 926 for storing programs and the like for taking tomographic images also works as an inspected eye information storage portion. In other words, the inspected eye information storage portion stores information about the eye or the person who owns the eye for use in subsequent re-inspection of the eye. A target position of the measurement optical system is stored with the person's information so that re-inspection of the eye may be performed at or near the same position to obtain consistent results. A monitor 928 is a display portion, and an input portion 929 is used for giving instruction to the personal computer, and is specifically formed of a keyboard and a mouse. A chin rest 323 is used for fixing the chin and the forehead of the person to be inspected so that the person's head is fixed and thus the person's eye to be inspected is easily fixed.

(Configurations of Measurement Optical System and Spectroscope)

Figure 2B:
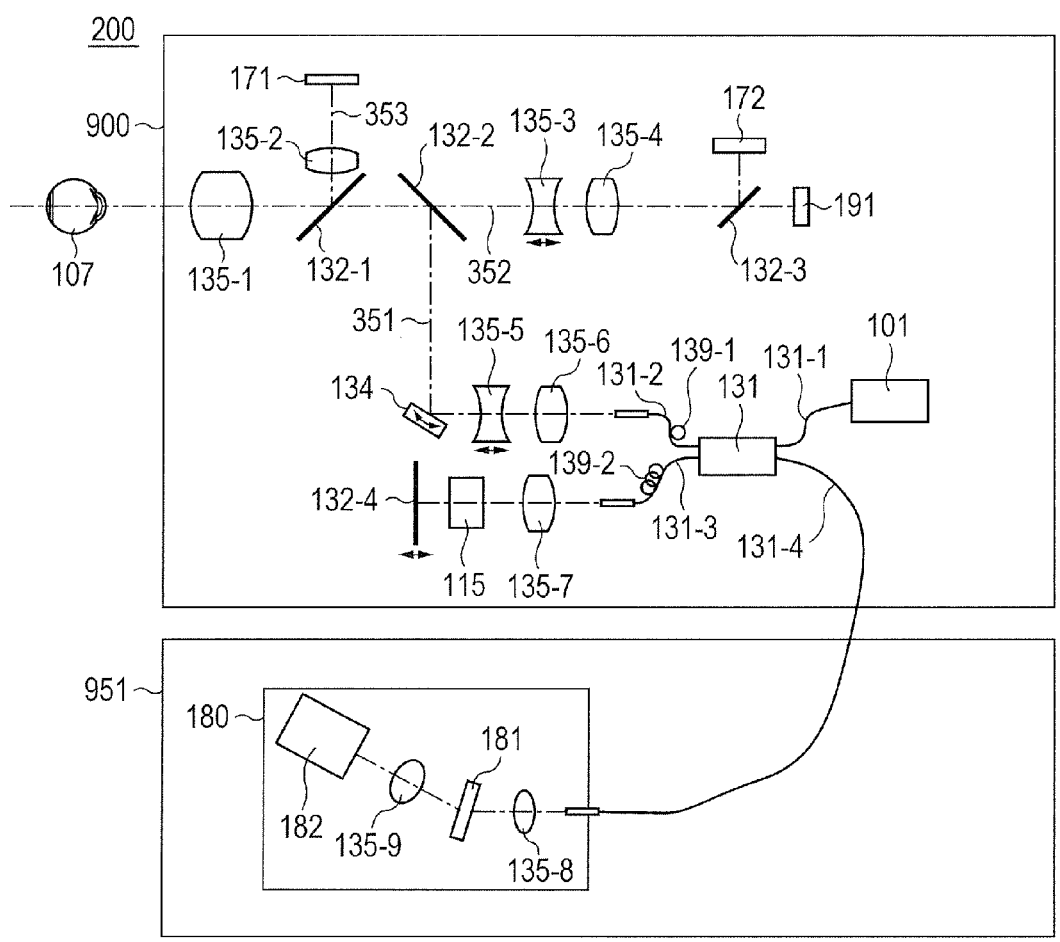
FIG. 2B is a schematic diagram of a configuration example of a measurement optical system and a spectroscope of the fundus inspection apparatus illustrated in FIG. 2A.

Configurations of the measurement optical system and the spectroscope of this embodiment are described with reference to FIG. 2B. First, an inside of the optical head 900 is described. An objective lens 135-1 is disposed to be opposed to an eye to be inspected 107. On the optical axis of the objective lens 135-1, a first dichroic mirror 132-1 and a second dichroic mirror 132-2 separate an input optical path into three optical paths in accordance with their wavelength bands: optical path 351 of an OCT optical system, optical path 352 for fundus observation and a fixation lamp, and optical path 353 for anterior ocular observation.

The optical path 352 is further split by a third dichroic mirror 132-3 into an optical path to a CCD 172 for fundus observation and an optical path to a fixation lamp 191 in accordance with their wavelength bands in the same manner as described above. Also on optical path 352, the optical head 900 includes lenses 135-3 and 135-4. The lens 135-3 is driven by a motor (not shown) for focusing of the fixation lamp and fundus observation. The CCD 172 has a sensitivity at a wavelength of illumination light (not shown) for fundus observation, specifically at a wavelength of approximately 780 nm. On the other hand, the fixation lamp 191 generates visible light so as to prompt the person to be inspected to stare.

In the optical path 353, there are disposed a lens 135-2 and an infrared CCD 171 for anterior ocular observation. This CCD 171 has a sensitivity at a wavelength of illumination light (not shown) for anterior ocular observation, specifically at a wavelength of approximately 970 nm.

The optical path 351 constitutes the OCT optical system as mentioned above, and is used for taking the tomographic image of the fundus of the eye to be inspected 107. More specifically, the optical path 351 is used for acquiring an interference signal for forming the tomographic image. The optical head 900 includes an XY scanner 134 for scanning the fundus with light. The XY scanner 134 is illustrated as a single mirror for simplification but is used for scanning in two directions of X and Y axes. The optical head 900 includes lenses 135-5 and 135-6, and the lens 135-5 is driven by a motor (not shown) so as to focus light from a light source 101 onto the fundus of the eye 107, the light emerging from a fiber 131-2 connected to an optical coupler 131. By this focusing operation in reverse, reflected light from the fundus of the eye 107 is focused as a spot on an end of the fiber 131-2 and thus enters the fiber 131-2.

Next, configurations of an optical path from the light source 101, a reference optical system, and the spectroscope are described.

The optical head 900 includes the light source 101 mentioned above, a mirror 132-4, a dispersion compensating glass 115, the above-mentioned optical coupler 131, single-mode optical fibers 131-1 to 131-4 connected and integrated to the optical coupler, and a lens 135-7. The base portion 951 includes a spectroscope 180.

These elements constitute a Michelson interferometer. The light emitted from the light source 101 passes through the optical fiber 131-1 and is split by the optical coupler 131 into the measuring light on the optical fiber 131-2 side and the reference light on the optical fiber 131-3 side. The measuring light irradiates the fundus of the eye to be inspected 107 as an observation target via the optical path 351 of the above-mentioned OCT optical system and is reflected or scattered by the retina to reach the optical coupler 131 via the same optical path.

On the other hand, the reference light passes through the optical fiber 131-3, the lens 135-7, and the dispersion compensating glass 115 inserted for adjusting dispersion between the measuring light and the reference light, so as to reach the mirror 132-4, and is reflected by the mirror 132-4. Then, the reference light returns along the same optical path and reaches the optical coupler 131.

The optical coupler 131 combines the measuring light with the reference light to give interference light. Here, the interference occurs when an optical path length of the measuring light becomes almost the same as an optical path length of the reference light. The mirror 132-4 is retained in an adjustable manner in an optical axis direction by a motor (not shown) and a drive mechanism (not shown), and hence the optical path length of the reference light can be adjusted to the optical path length of the measuring light that varies depending on the eye to be inspected 107. The interference light is guided to the spectroscope 180 via the optical fiber 131-4.

In addition, a polarization adjustment portion 139-1 of the measuring light side is disposed in the optical fiber 131-2. A polarization adjustment portion 139-2 of the reference light side is disposed in the optical fiber 131-3. The polarization adjustment portions include some parts in which the optical fiber is looped, and the looped part is turned about a longitudinal direction of the fiber so that the fiber is twisted. Thus, polarized states of the measuring light and the reference light can be adjusted respectively. In this apparatus, the polarized states of the measuring light and the reference light are adjusted and fixed in advance.

The spectroscope 180 is formed of lenses 135-8 and 135-9, a diffraction grating 181, and a line sensor 182.

The interference light emerged from the optical fiber 131-4 becomes collimated light via the lens 135-8, and is then diffracted by the diffraction grating 181 so as to form images on the line sensor 182 via the lens 135-9.

Next, a periphery of the light source 101 is described. The light source 101 is a super luminescent diode (SLD) that is a typical low coherent light source. For instance, the center wavelength is 855 nm, and the wavelength band width is approximately 100 nm. Here, the band width is an important parameter because it affects a resolution of the acquired tomographic image in the optical axis direction. In addition, the SLD is selected as a type of the light source here, but it is sufficient when the light source can emit low coherent light. It is possible to use an amplified spontaneous emission (ASE) source or the like. As to the center wavelength, near infrared light is suitable in view of measuring an eye. In addition, because the center wavelength affects the resolution of the acquired tomographic image in a lateral direction, it is desired that the wavelength be as short as possible. In this embodiment, because of both of these reasons, the center wavelength is set to 855 nm.

The Michelson interferometer is used in this embodiment, but a Mach-Zehnder interferometer may be used. In accordance with a light intensity difference between the measuring light and the reference light, it is desired to use the Mach-Zehnder interferometer when the light intensity difference is large, and to use the Michelson interferometer when the light intensity difference is relatively small.

(Method of Taking the Tomographic Image)

A method of taking the tomographic image using the fundus inspection apparatus 200 is described. The fundus inspection apparatus 200 can take the tomographic image of a desired part of the fundus of the eye to be inspected 107 by controlling the XY scanner 134.

Figure 5A:
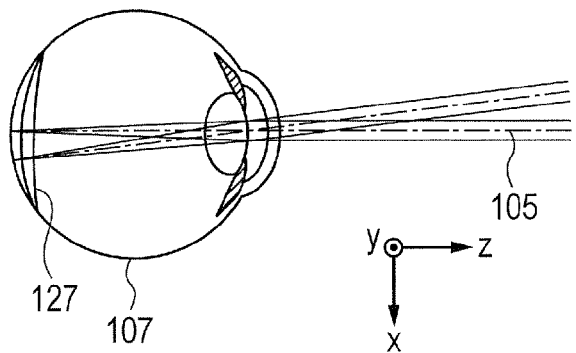
FIGS. 5A, 5B and 5C are diagrams illustrating relationships between an eye to be inspected and light rays for observation when a new alignment position is obtained in the first embodiment.

First, measuring light 105 (see FIG. 5A) scans in an x direction in FIG. 5A so that the line sensor 182 (FIG. 2B) photographs information a predetermined number of times in a photographing range of the fundus in the x direction. The fast Fourier transform (FFT) is performed on a luminance distribution obtained on the line sensor 182 at a certain position in the x direction, and a linear luminance distribution obtained by the FFT is converted into density or color information to be displayed on the monitor 928. This converted information is referred to as an A-scan image. A two-dimensional image on which multiple or a plurality of A-scan images are arranged is referred to as a B-scan image. After multiple A-scan images are taken for organizing one B-scan image, the scan position in a y direction is moved, and the scanning in the x direction is performed again so that multiple or a plurality of B-scan images are acquired.

The multiple B-scan images or a three-dimensional tomographic image organized from the multiple B-scan images is displayed on the monitor 928 so as to be used for diagnosis of the eye by the inspector.

(Flow of Taking the Tomographic Image)

Figure 1:
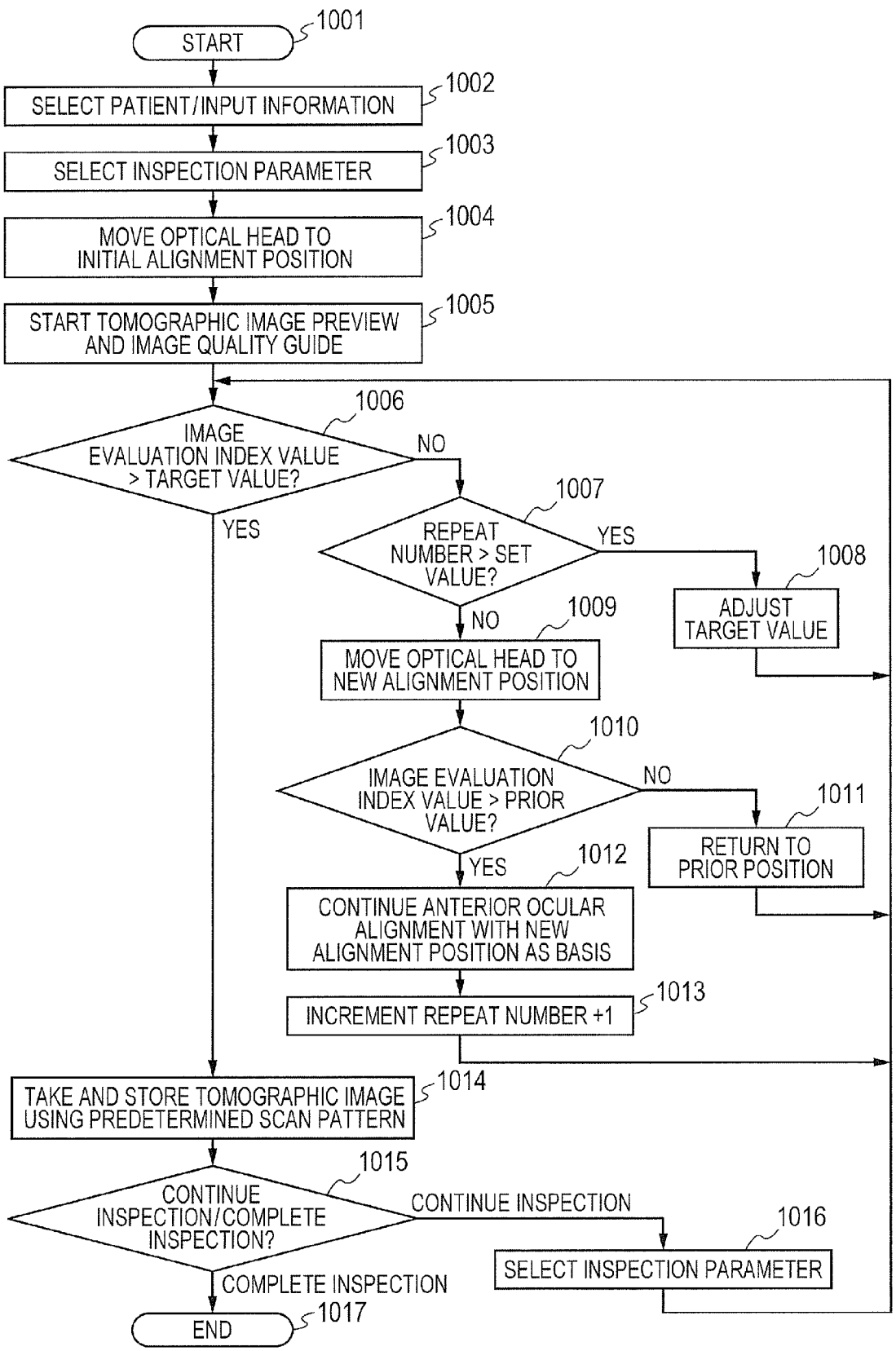
FIG. 1 is a flowchart illustrating how to take an image according to a first embodiment of the present invention.

A photographing flowchart is illustrated in FIG. 1 and is described in the order of the illustrated steps.

In Step 1001, the photographing is started. The personal computer 925 executes a program for photographing so that a screen for photographing (see FIG. 6 and its associated description below) is displayed on the monitor 928. Simultaneously, the XY scanner 134 is activated. The process proceeds to Step 1002 automatically.

In Step 1002, the monitor 928 displays a patient information input screen, and the inspector selects a patient or inputs patient information for a new patient. By the inspector's operation (such as a click of an OK button displayed on the patient information input screen using a mouse), the process proceeds to Step 1003.

In Step 1003, the monitor displays an inspection parameter selection screen, and the inspector sets inspection parameters such as the left or right eye to be inspected, a range of tomographic images, the number of tomographic images taken, and the number of A-scan images to be included in the B-scan image. These settings for taking tomographic images are referred to as a scan pattern. Then, by the inspector's operation (such as a click of an OK button displayed on the inspection parameter selection screen using the mouse), the process proceeds to Step 1004.

In Step 1004, the control unit (the personal computer) 925 moves the optical head 900 to an initial alignment position.

Figure 6:
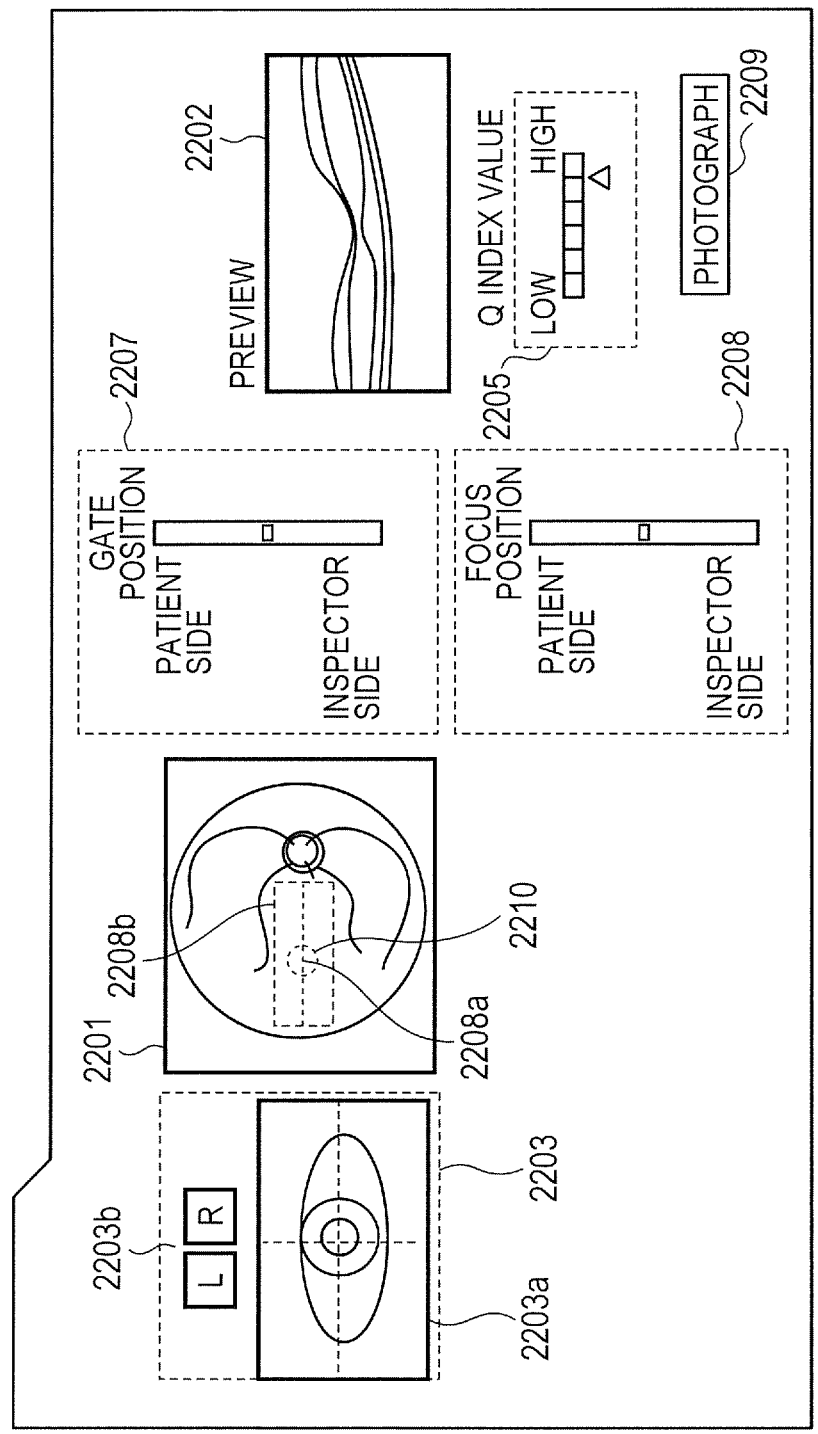
FIG. 6 is a diagram illustrating a screen for alignment in the first embodiment.

The monitor 928 displays a screen for taking tomographic images such as that illustrated in FIG. 6. In this step, the anterior ocular image and the fundus image are displayed. An anterior ocular image monitor 2203 includes an anterior ocular image 2203a, and a left/right selection button 2203b for the eye to be inspected, which also has a function of displaying by brightness which eye is selected. "2201" represents a fundus image, "2208a" represents a position of the B-scan image of a tomographic image preview described later, and "2208b" represents a tomographic image photographing range selected in Step 1003. Here, as an example, the position 2208a is positioned on a macula lutea 2210.

Figure 3A:
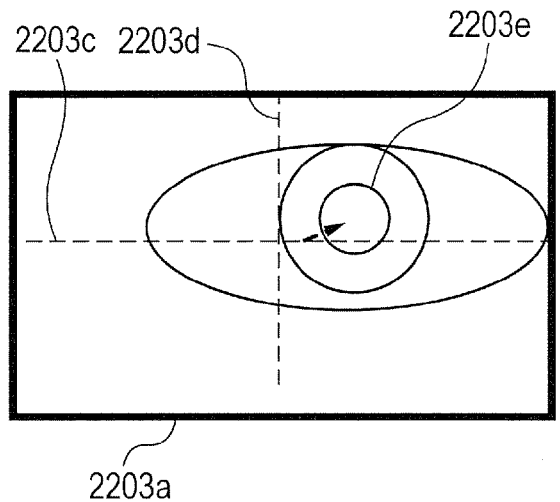
FIGS. 3A, 3B and 3C are diagrams illustrating anterior ocular images obtained in each operation during alignment in the first embodiment.
Figure 3B:
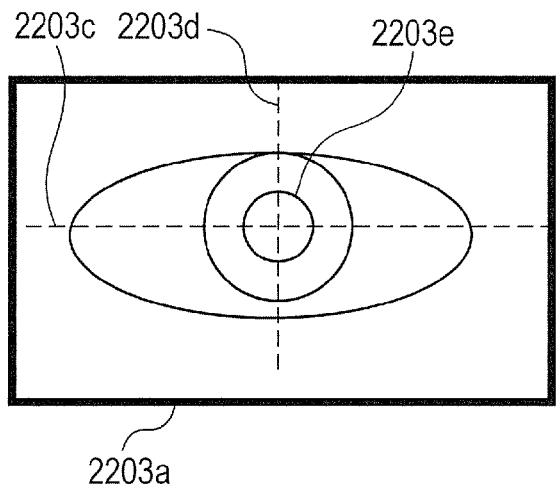

In this step, the optical head 900 is moved to a measurement start position depending on the left or right eye to be inspected, and the CCD 171 for anterior ocular observation takes an image of the anterior ocular segment of the eye to be inspected 107. FIG. 3A illustrates an example of the image, and the center of the image (indicated as an intersection of indicators 2203c and 2203d) is aligned with the optical axis of the measurement optical system of the optical head 900. As to an XY direction, the control unit moves the optical head 900 so that the center of a pupil 2203e is aligned with the image center position. Alignment may be sufficient when the positioning between the optical head 900 and the center of the anterior ocular image is performed relatively. Therefore, the configurations of the control unit 925, the stage portion 950, and the like for moving the optical head 900 function together as a relative position changing unit for changing the relative position therebetween, and it is also possible to adopt a configuration in which the anterior ocular segment side is moved. An example of the image of the moved anterior ocular segment is illustrated in FIG. 3B, in which the center of the pupil 2203e is aligned with the image center. As to a Z direction, the optical head 900 is moved for adjustment based on a size or the like of a bright spot (not shown) on the image projected to the anterior ocular segment. For instance, the adjustment in the Z direction is performed so that a size of the bright spot becomes smallest.

A position of the optical head 900 after the alignment in this step is known as the initial alignment position. The center of the pupil 2203e is extracted by the image processing. In other words, the initial alignment is performed based on an image of the anterior ocular segment of the eye to be inspected obtained by the optical head 900 at the beginning.

After that, the process proceeds to Step 1005 automatically.

In Step 1005, the tomographic image preview and an image quality guide are displayed.

The personal computer 925 organizes the tomographic image at the position 2208a (shown in FIG. 6) from a signal from the line sensor 182 and displays the image as illustrated by 2202 in FIG. 6. In addition, an indicator 2205 indicates a Q index value that is the image quality guide of the displayed tomographic preview image 2202. In other words, the monitor 928 as the display portion visualizes and displays an image evaluation index of the tomographic image or a value thereof. As this indicator is positioned closer to the right end, the Q index value of the image becomes higher, and hence the quality of the image as displayed visually is improved. Here, the Q index is an OCT image evaluation index and indicates a ratio of pixels effective for diagnosis, in a histogram of the image. This Q index is calculated and is compared with a target value or a value at another alignment position. The operation described above is performed by a region functioning as a program module for executing the operation as an evaluation index calculation unit and an image comparing unit in the personal computer (movement control unit) 925. The program for executing the operation is integrated with the program for photographing described above and is executed by the personal computer 925.

A method of calculating the Q index is described in the following document:

"A new quality assessment parameter for optical coherence tomography, British Journal of Ophthalmology 2006, vol. 90, pp. 186-190"

Here, the Q index value is used as the image quality guide, but the following other image evaluation indices may be used, or indeed, a further image evaluation index may be used that is not disclosed here.

(1) SNR (signal to noise ratio) as an indicator that has been often used conventionally, which indicates a ratio between a maximum value of the image luminance value (i.e. the signal) and a luminance value of background noise.

Figure 4A:
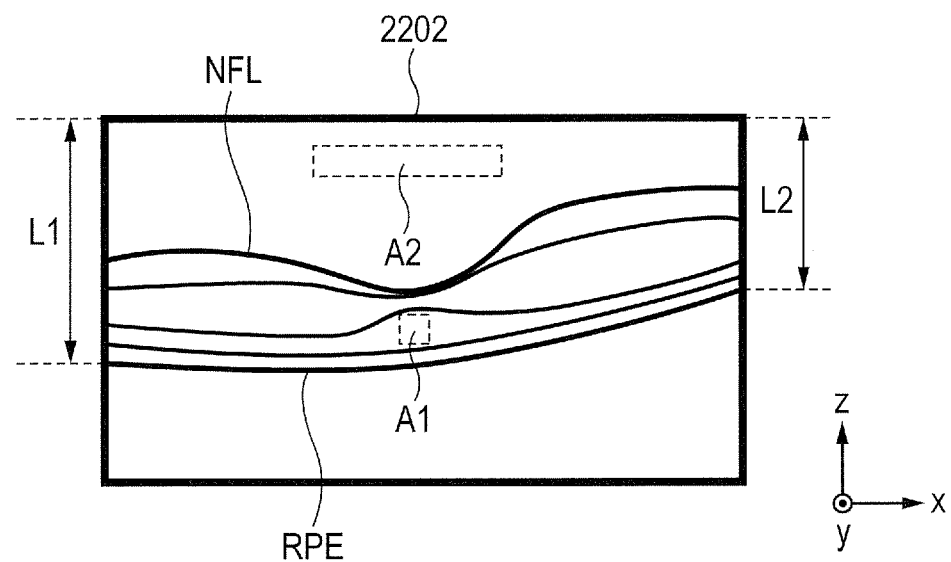
FIGS. 4A and 4B are diagrams illustrating preview images of tomographic images before and after the alignment in the first embodiment.

(2) A local image contrast, which is a contrast derived from an average luminance value in a local region of the retina and an average luminance value of the background. An example thereof is described with reference to FIG. 4A. FIG. 4A illustrates a preview image of the tomographic image displayed in the tomographic preview image 2202. "A1" is a partial region of an outer nuclear layer (ONL) that is relatively dark in the retina and "A2" is a partial region of the background portion. From the average luminance values of the two regions, the contrast is calculated.

The local contrast is not limited to the contrast between the ONL and the background, but may be a contrast between layers that are necessary for diagnosis, or a contrast between a layer and the background, which may be set so that the inspector can select the relevant layer.

The calculation of the local image contrast requires segmentation for discriminating the ONL or the like so as to recognize a region.

In this step, there are performed the optical path length adjustment of the reference optical path by moving the mirror 132-4, the focusing of the fundus image by the lens 135-3, and the focusing of the tomographic image by the lens 135-5. These operations are also adjusted automatically, but as illustrated in FIG. 6, a gate position adjustment slider 2207 and a focus position adjustment slider 2208 are disposed on the screen so that the inspector can perform fine adjustment after the automatic adjustment. Next, the process automatically proceeds to Step 1006.

In Step 1006, it is determined whether or not the Q index value that is the above-mentioned image evaluation index value calculated by the calculation unit is higher than a predetermined target value. As described above, when it is determined by an image evaluation unit that the image evaluation index value is higher than the target value, namely, that the image is good, the process proceeds to Step 1014. When it is determined that the image evaluation index value is the target value or lower, namely, that the image is not good, the process proceeds to Step 1007.

In Step 1007, it is determined whether or not the number of times of repeating the alignment fine adjustment routine of Steps 1006 to 1012 is larger than a set value. When the number of times of repeating is larger than the set value, the process proceeds to Step 1008 in which the target value of the image evaluation index is corrected to be a smaller value, and the process returns to Step 1006. This is because there is a case where a high image evaluation index value is not achieved in any position depending on the eye to be inspected, and it is necessary to settle on the automatic alignment action in that case. When the number of times of repeating is the set value or lower, the process proceeds to Step 1009.

In Step 1009, the optical head 900 is moved to the new alignment position. Before the movement, the automatic alignment function for the anterior ocular is temporarily stopped.

Here, a method of deriving the new alignment position is described. For instance, there is a case where the tomographic image is tilted on the screen. This case is described with reference to FIGS. 5A to 5C as an example of photographing the vicinity of the macula lutea.

Figure 5B:
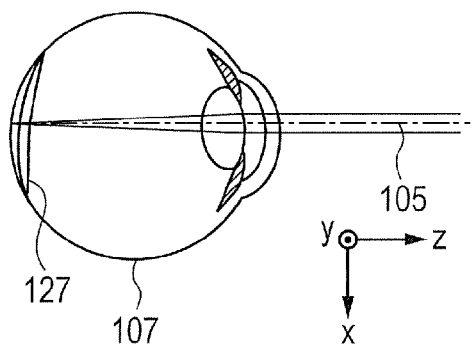

In FIG. 5A, if the axis of the eye to be inspected 107 is not tilted with respect to the measuring light 105, when photographing the macula lutea center by fixation, incident light is almost perpendicular to the vicinity of the macula lutea of a retina 127. Therefore, intensity of return light is high so that high signal intensity can be obtained. On the other hand, in the case of the eye to be inspected 107 having a tilted axis, the vicinity of the macula lutea is tilted from the optical axis of the incident light when the incident light 105 reaches the retina 127 as illustrated in FIG. 5B. Therefore, the signal intensity becomes low, and simultaneously, the tomographic image is tilted as illustrated in FIG. 4A in many cases. In this case, the Q index as the image evaluation index also becomes a low value. That is, movement of the measurement system is response to tilt is the same as movement of the measurement system in response to a low evaluation index value.

Figure 4B:
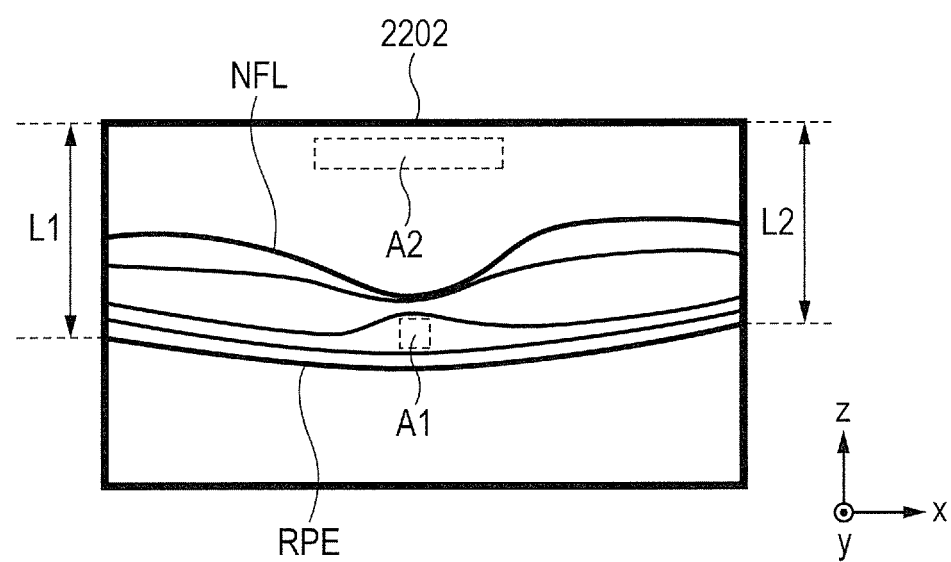
Figure 5C:
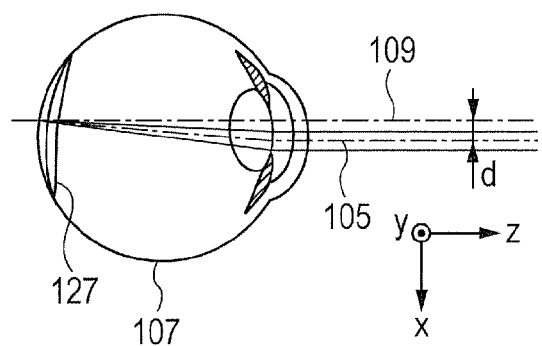

For instance, by the above-mentioned segmentation, a distance from an image end portion of a pigment epithelium (RPE) layer having highest luminance in the tomographic image or a distance from a boundary at an image upper portion is compared so as to move the optical head 900. Specifically, the optical head 900 is moved so that a distance L1 between an image upper left portion (gate position) and the RPE layer at the left end in FIG. 4A becomes substantially equal to a distance L2 between an image upper right portion and the RPE layer at the right end. In this way, in this embodiment, a value indicating a tilt of the tomographic image is determined when the personal computer 925 determines the distance L1 and the distance L2. In other words, the personal computer 925 determines the tilt of the tomographic image. Each of the distance L1 and the distance L2 is a distance between the tomographic image and the image end portion included in the image obtained by the personal computer 925. An example after the movement is illustrated in FIGS. 4B and 5C, which is a case where the optical head 900 is moved by d from the initial alignment position in the X direction. The incident light 105 becomes substantially perpendicular to the vicinity of the macula lutea, and the distances L1 and L2 on both ends are substantially the same as illustrated in FIG. 4B. In this condition, the Q index value becomes high in many cases. In other words, in the adjustment of a movement amount of the optical head 900 as the measurement optical system, the personal computer 925 calculates the adjustment amount based on a position of a portion on the tomographic image, which can be easily extracted as a predetermined characteristic portion with high luminance by segmentation, such as the both ends of the RPE layer in the tomographic image, namely, based on a distance from the gate position on the tomographic image. In other words, the personal computer 925 calculates the distance L1 and the distance L2, and therefore the personal computer 925 corresponds to an example of a tilt calculation unit for calculating a tilt of the tomographic image.

Note that the personal computer 925 stores a table in which a moving amount and moving direction of the optical head 900 are associated with the value designated as the tilt. The personal computer 925 determines the moving amount and the moving direction of the optical head 900 on the basis of the table. In addition, the personal computer 925 controls the movement of the optical head 900 through the stage 950 in accordance with the determined moving amount and direction.

Here, an example has been described, in which automatic tilt correction is performed based on a distance between the image upper portion and the RPE layer, but the automatic tilt correction may be performed based on a distance between the image upper portion and a nerve fiber layer (NFL) when the NFL is considered in a case of glaucoma inspection or the like. In other words, the layer used for the tilt correction is not limited to the RPE layer. It is possible to use a position of a layer other than the RPE layer for correction of the tilt of the tomographic image. In the present invention, the relative position changing unit performs the change of a relative position between the eye to be inspected and the tomographic image acquiring unit based on the tilt of the tomographic image so that the tilt is decreased.

In addition, the distance L1 between the RPE layer and the image upper portion at the left end of the tomographic image, and the distance L2 between the RPE layer and the image upper portion at the right end of the tomographic image are determined so as to derive the tilt of the tomographic image, but this method is not a limitation. For instance, it is possible to derive the tilt from distances between each position of at least two points on a predetermined layer and an image end portion (e.g. the image upper end or the image lower end). In other words, the tilt may be derived from distances between each position of at least two points on a predetermined layer and a predetermined position elsewhere on the image (for example, an image end portion). Here, the image end portion means an end portion of the photographing range.

In addition, it is possible to derive the tilt from a difference between coordinates or positions of at least two points on a predetermined layer. For instance, in order to correctly grasp the tilt of the tomographic image, it is possible to set the recess (fovea centralis) of the macula lutea as the center, and to set two points on a predetermined layer having the same distance from the center. Then, the above-mentioned distances L1 and L2 may be set as distances between each of the two points and the image upper end or the image lower end. It is preferred to change the relative position between the eye to be inspected and the tomographic image acquiring unit so that the distances L1 and L2 are equal to each other.

In FIG. 4A, only the X direction is illustrated (the tomographic image is in the Z-plane with a tilt in the X-direction), but the tilt correction may be performed in the X or Y direction, or both in the X and Y directions. In order to determine movement in the Y direction, it is necessary to photograph the tomographic image preview as the tomographic image in the Y direction.

In this state, the process automatically proceeds to Step 1010.

In Step 1010, the image evaluation index value is compared with the value before the movement in Step 1009 (i.e. the prior value). When the image evaluation index value is smaller than the prior value, the process proceeds to Step 1011. When the image evaluation index value is larger than the prior value, the process proceeds to Step 1012.

In Step 1011, the optical head 900 is moved to the prior position. In this case, the movement amount may be changed in this step so as not to be the same as the current movement amount, by multiplying a coefficient for weighting a calculated correction amount. For instance, it is possible to multiply the correction amount calculated from the tilt by a coefficient of 0.5 to obtain the result as a real movement amount. Further, it is considered that the image evaluation index is decreased due to a factor other than the tilt, and hence it is possible to set it so as to move by a fixed step amount for the next time.

In Step 1012, in the example described above, the anterior ocular automatic alignment is started at a position apart from the pupil center by the distance d (in FIG. 5C), namely, at a new alignment position, and this photographing operation is continued. Thus, it is possible to photograph an image while maintaining a good state of acquired images even in tomographic photography with relatively long photographic time. The distance d from the pupil center indicating the new alignment position is temporarily stored.

Figure 3C:
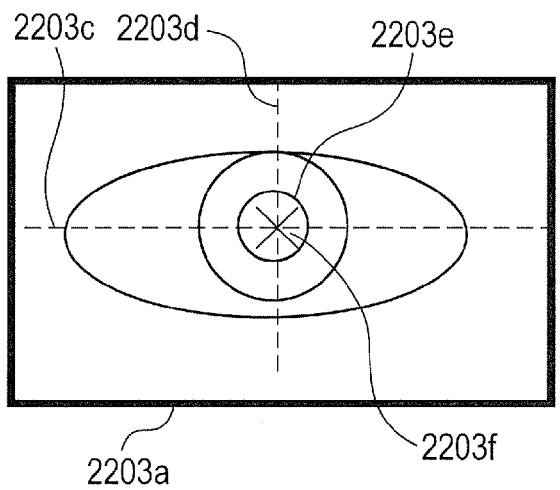

FIG. 3C illustrates the anterior ocular image 2203a in this case. A mark 2203f indicating the new alignment position is displayed at the position at a distance d from the center of the pupil 2203e so as to inform the inspector that the alignment is continued at the new position. After that, the process automatically proceeds to Step 1013.

In Step 1013, the number of times of repeating is incremented by one, and the process returns to Step 1006.

Then, Steps 1006 to 1013 are repeated, and finally the process proceeds to Step 1014.

In Step 1014, the tomographic image is photographed by the scan pattern set in Step 1003, and simultaneously, the tomographic image is stored in a storage device in the personal computer 925. This storing operation may be performed automatically or by clicking a photograph button 2209 (shown on FIG. 6) with the mouse. The process automatically proceeds to Step 1015.

In Step 1015, a screen for selecting to continue the inspection or to finish the inspection is displayed, and the inspector selects one of the continuing and the finishing. In addition, it is possible to display the photographed tomographic image at this stage. When the inspection is to be continued, the process proceeds to Step 1016 in which the inspection parameters for the next photographing are set, and the process returns to Step 1006. When the inspection is to be finished, the process proceeds to Step 1017 in which the inspection is finished.

The flow of photographing by the fundus inspection apparatus of this embodiment has been described hereinabove.

The new alignment position stored every time when being updated is stored in the hard disk 926 in the personal computer 925 together with the patient information (i.e. the eye inspection information which is stored in the inspected eye information storage portion of the hard disk) when the tomographic image is stored. Thus, when re-inspection is performed for inspecting the same eye, the target position as the initial alignment position in the adjustment is set as the new alignment position. After the optical head 900 is moved to the initial target position, the automatic alignment is started from the position so that the automatic alignment can be started from a state having a high Q index value. In the example of FIG. 5A, the automatic alignment can be started not from the pupil center but from the position separated from the pupil center by the distance d. Therefore, the load on the person to be inspected can be reduced by shortening the inspection time.

As described above, according to the present invention, it is possible to automatically find the position at which a good tomographic image can be photographed so that the operation of the inspector can be simplified.

In addition, because the positional relationship between the eye to be inspected and the image acquiring unit for the eye to be inspected is automatically adjusted so that a good tomographic image can be photographed, the operation of the inspector can be simplified.

Further, a good tomographic image can be automatically photographed, and the automatic alignment for acquiring good tomographic images can be continuously performed.

The use of the apparatus is easy for the inspector, and the load on the person to be inspected can be reduced because the inspection time is shortened.

In addition, because the image evaluation index of the tomographic image is visualized and displayed, it is easy for the inspector to determine whether or not the tomographic image is good.

In addition, when the tomographic image is stored, the adjustment target position is stored for each person to be inspected. When the inspected person information is retrieved for re-inspection, the adjustment target position is simultaneously retrieved and is set as the initial adjustment target position for the re-inspection. Thus, alignment time for the re-inspection can be shortened, and hence the load on the person to be inspected can be further reduced.

In a case in which the alignment position is automatically adjusted so as to decrease the tilt of the tomographic image as described above, information such as a message designating the execution of automatic adjustment may be indicated on the monitor 928. In this way, it becomes possible to understand whether the shift of the alignment position from the pupil center is caused from failure of the apparatus or not.

Other than the indication of the message designating the execution of the automatic adjustment of the alignment position, means such as a sound of alarm for informing the inspector of the execution of the automatic adjustment of the alignment position can be used.

In addition, a difference between the Q index values before and after the execution of the automatic adjustment of the alignment position for decreasing the tilt of the tomographic image can be indicated, or a value of tilt after adjustment can be indicated. As the result of such indication, the inspector can understand the execution level of the automatic adjustment of the alignment position. The indication of the shift amount of the alignment position from the pupil center may provide the same effect as that obtained from above described indication.

Furthermore, the alignment position which is result of the execution of the automatic adjustment of the alignment position may be changed to the initial alignment position or, before the execution of the automatic adjustment of the alignment position, by an instruction of the inspector. In this way, the inspector can confirm a tilt level of the tomographic image at a conventional alignment position. Such change-over operation can be executed by memorizing a status of the apparatus at a time of executing the alignment operation for the pupil center and a status of the apparatus at a time of executing the alignment operation for a position shifted from the pupil center. Such instruction may be performed through a switch or the like capable of such changeover operation, which is indicated on the monitor 928, or an actual or physical switch provided on the apparatus.

Other Embodiments

In addition, the present invention can be realized also by performing the following process. Specifically, software (program) for realizing the functions of the above-mentioned embodiment is supplied to a system or an apparatus via a network or various storage media, and a computer (CPU or MPU) of the system or the apparatus reads and executes the program.

Note that, the disclosed technology is not limited to the embodiment described above, but can be embodied with various modifications within the scope of the claims and without departing from the spirit of this embodiment.

For instance, the display portion 928 may display a GUI (graphical user interface) indicating photographing the tomographic image of the macula lutea. When the inspector designates this GUI, the macula lutea may be automatically detected from the fundus image of the eye to be inspected so as to acquire the tomographic image of the macula lutea. It is possible to acquire the tomographic image of the macula lutea automatically after extracting the macula lutea or to acquire the tomographic image of the macula lutea in accordance with an inspector's instruction.

In addition, the tomographic image to be acquired is not limited to the tomographic image of the macula lutea, but may be another tomographic image such as a tomographic image of an optical disk.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-236014, filed Oct. 27, 2011, which is hereby incorporated by reference herein in its entirety.

What is claimed is:
1. An ophthalmologic apparatus, comprising:
a tomographic image acquiring unit configured to acquire a tomographic image of a fundus of an eye to be inspected, the tomographic image being a two-dimensional image including a depth direction of the fundus of the eye to be inspected;
an evaluation index calculation unit configured to calculate an image evaluation index of the tomographic image;
a tilt calculation unit configured to calculate a tilt of a first tomographic image acquired by the tomographic image acquiring unit;
a relative position changing unit configured to change a relative position between the tomographic image acquiring unit and the eye, by relatively moving the tomographic image acquiring unit in a plane perpendicular to an optical axis of the tomographic image acquiring unit, based on the tilt of the first tomographic image, so as to reduce the tilt of a second tomographic image acquired by the tomographic image acquiring unit, wherein the second tomographic image is acquired after the first tomographic image is acquired; and
a display control unit configured to cause a display unit to display information that the relative position is changed by the relative position changing unit, wherein the tilt of the second tomographic image is reduced such that the image evaluation index of the second tomographic image is greater than the image evaluation index of the first tomographic image.

2. An ophthalmologic apparatus according to claim 1, wherein the tilt calculation unit is configured to calculate the tilt based on a position of a predetermined layer in the tomographic image.

3. An ophthalmologic apparatus according to claim 1, wherein the tilt calculation unit is configured to calculate the tilt based on distances between each of two points on a predetermined layer and a predetermined position in the tomographic image.

4. An ophthalmologic apparatus according to claim 3, wherein the relative position changing unit is configured to change the relative position between the tomographic image acquiring unit and the eye so that the distances between the each of the two points on the predetermined layer and the predetermined position in the tomographic image are equal to each other.

5. An ophthalmologic method comprising:
acquiring a tomographic image of a fundus of an eye to be inspected using a tomographic image acquiring means, the tomographic image being a two-dimensional image including a depth direction of the fundus of the eye to be inspected;
calculating an image evaluation index of the tomographic image;
calculating a tilt of a first tomographic image acquired using the tomographic image acquiring means;
changing a relative position between the tomographic image acquiring means and the eye to be inspected, by relatively moving the tomographic image acquiring means in a plane perpendicular to an optical axis of the tomographic image acquiring means, based on the tilt of the first tomographic image, so as to reduce the tilt of a second tomographic image acquired by the tomographic image acquiring means,
wherein the second tomographic image is acquired after the first tomographic image is acquired; and
causing a display unit to display information of the changed relative position,
wherein the tilt of the second tomographic image is reduced such that the image evaluation index of the second tomographic image is greater than the image evaluation index of the first tomographic image.

6. An ophthalmologic apparatus according to claim 1, further comprising a table in which the tilt of the tomographic image is associated with a moving amount of the tomographic image acquiring unit, wherein the relative position changing unit determines the moving amount of the tomographic image acquiring unit based on the table.

7. An ophthalmologic method according to claim 5, wherein in the step of calculating the tilt, the tilt is calculated based on a position of a predetermined layer in the tomographic image.

8. An ophthalmologic method according to claim 5, wherein in the step of calculating the tilt, the tilt is calculated based on distances between each of two points on a predetermined layer and a predetermined position in the tomographic image.

9. An ophthalmologic method according to claim 8, wherein in the step of changing the relative position, the relative position between the tomographic image acquiring means and the eye is changed so that the distances between the each of the two points on the predetermined layer and the predetermined position in the tomographic image are equal to each other.

10. An ophthalmologic method according to claim 5, wherein in the step of changing the relative position, a moving amount of the tomographic image acquiring means is determined based on a table in which the tilt of the tomographic image is associated with a moving amount of the tomographic image acquiring means.

11. A non-transitory tangible medium having recorded thereon a program for causing a computer to perform steps of the ophthalmologic method according to claim 5.

12. An ophthalmologic apparatus according to claim 3, wherein the predetermined layer is a retinal pigment epithelium layer.

13. An ophthalmologic apparatus according to claim 3, wherein the predetermined layer is a nerve fiber layer.

14. An ophthalmologic apparatus according to claim 1, wherein the image evaluation index is a Q index.

15. An ophthalmologic method according to claim 5, wherein the image evaluation index is a Q index.

* * * * *